United States Patent [19]
Yamanaka et al.

[11] 4,167,518
[45] Sep. 11, 1979

[54] NON-ALLERGENIC LANOLIN COMPOSITIONS

[75] Inventors: Makoto Yamanaka, Koganei; Tsuruo Mikata, Kashiwa; Satoshi Takano, Funabashi; Kikuhiko Okamoto, Koshigaya; Fumio Saito, Tokyo, all of Japan

[73] Assignee: Kao Soap Co., Ltd., Tokyo, Japan

[21] Appl. No.: 717,403

[22] Filed: Aug. 24, 1976

[30] Foreign Application Priority Data

Oct. 9, 1975 [JP] Japan ................................ 50/122331

[51] Int. Cl.2 ........................ A61K 7/48; A61K 47/00

[52] U.S. Cl. ............................ 260/397.25; 260/397.2; 260/419; 568/917

[58] Field of Search ................. 260/419, 428.5, 643 F, 260/643 G, 397.25, 397.2; 424/312, 365

[56] References Cited

U.S. PATENT DOCUMENTS

| | | | |
|---|---|---|---|
| 2,524,414 | 10/1950 | Wolfrom | 260/643 G |
| 2,913,501 | 11/1959 | Cahill | 260/643 G |

*Primary Examiner*—John F. Niebling
*Attorney, Agent, or Firm*—Oblon, Fisher, Spivak, McClelland & Maier

[57] ABSTRACT

A non-allergenic lanolin or a derivative thereof which does not contain any substances which have an Rf value of less than 0.38 with a chloroform solvent or less than 0.14 with a benzene solvent, in thin layer chromatography using magnesium silicate having a thickness of 0.25 mm as the adsorbent.

4 Claims, No Drawings

NON-ALLERGENIC LANOLIN COMPOSITIONS

BACKGROUND OF THE INVENTION

1. Field of the Invention

2. Description of the Prior Art

This invention relates to non-allergenic lanolin and derivatives thereof, and to a process for producing the same.

Lanolin is a higher fatty acid ester with a higher alcohol or sterol. The main fatty acid component includes the normal-, iso- and anteiso-isomer of an alkane acid,and an $\alpha$- and W-hydroxy acid, and therefore has a total of nine chemical forms. On the other hand, the alcohol component includes six varieties chemical forms which are normal-, iso- and anteiso-isomer of a mono-alcohol and a $\alpha$, $\beta$-diol, and several kinds of sterols.

It has been postulated that lanolin is a combination of the above alchols and acids, or a polymerized product thereof, in addition it contains several percent of substances, the structures of which remain unknown. Thus, lanolin is distinguished by the fact that is has no main component, but does have a sterol content of about 30% which corresponds to the major component.

Hitherto, lanolin has been widely used as a base for drug ointments and as a base for cosmetic creams and lotions however, it has very often induced an allergy at an occurrence frequency ranging from 1 to 18% in subjects.

It has been reported that the lanolin-induced allergy was observed with the same or more frequency as found with allergens such as nickel, chromium, p-phenylenediamine and the like, but less frequently observed than with formaldehyde.

Concerning the lanolin-induced allergy, Marcus at first reported some results with the use of a lanolin alcohol-combined cream as a test compound in 1922, but he did not refer at all to what really acted as the allergen in the test compound.

Thereafter, Sezary carried out many experiments with lanolin in 1936, but he could not find any components of lanolin capable of acting as an allergen, because of its highly complicated chemical structure, and merely cited a general term of lanolin compound as an allergen.

Fanburg first estimated lanolin alcohol to be an allergen in 1940. Subsequently, many investigators made a large number of studies on lanolin, lanolin alcohol and lanolin derivatives over a period of 30 years. Notwithstanding their continued efforts, the substance acting as the allergen still remains unknown. This is due to the difficulty of judgment of the allergy tests and the complicated chemical composition of lanolin.

SUMMARY OF THE INVENTION

In view of the situation, the present inventors have energetically investigated the elimination of the allergen from lanolin, and as a result haul found that any substances having characteristic values of Rf, induce allergy. Hence non-allergenic lanolin and derivatives thereof can be obtained by removing the above substances, however, we could not clarify what compounds really act as the allergen.

Based on this finding, this invention has been accomplished.

DETAILED DESCRIPTION OF THE PREFERRED EMBODIMENTS

The object of this invention may be achieved by eliminating substances having characteristic values of Rf less than 0.38 (developer: chloroform) or less than 0.14 (developer: benzene) in thin layer chromatography with the use of FLORISIL (Trademark of Florisin Co., Ltd., The United States of America) as an adsorbent having a thickness of 0.25 mm from lanolin and derivatives thereof. The Rf value represents the proportion of the total length of climb of a solution that is reached by a spot characteristic of one of the constituents present.

Lanolin and derivatives thereof, from which the allergen can be eliminated by column chromatography is described more specifically below, but include, for example, lanolin, lanolin wax, liquid lanolin, hydrogenated lanolin, acetylated lanolin alcohol, lanolin fatty acid ester and the like.

In order to remove the allergen from lanolin and the derivatives thereof according to the present invention, lanolin and its derivatives are subjected to chromatography with the use of a column packed with adsorbents such as fuller's earth, activated magnesia, activated carbon, alumina, silicic acid, magnesium silicate and the like, and eluted with a non-polar solvent and the eluates obtained by elution with the non-polar solvent are collected.

Magnesium silicate (for example FLORISIL) may be preferably used as an adsorbent, and the non-polar solvents may be selected from such organic solvents as n-hexane, benzene, toluene, petroleum ether, cyclohexane, carbon tetrachloride, chloroform and the like. These solvents may be used singly or in combination.

For the purpose of facilitating distillation after elution, odor and, above all toxicity benzene and petroleum ether may be favorably used.

The thus obtained non-allergenic lanolin may be further converted to the various non-allergenic lanolin derivatives according to any known methods.

Therefore, the non-allergenic lanolin and derivatives thereof obtained according to the present invention include lanolin and derivatives thereof do not contain any substances having characteristic values of Rf, and all non-allergenic lanolin derivatives derived from the above non-allergenic lanolin, such as hydrogenated lanolin, acetylated lanolin, ethoxylated lanolin, lanolin alcohol, acetylated lanolin alcohol, ethyoxy lanolin alcohol, ethoxylated and acetylated lanolin alcohol, ethoxylated hydrogenated lanolin, ethoxylated and propoxylated hydrogenated lanolin, lanolin fatty acid, lanolin fatty acid ester, lanolin fatty acid polyethylene glycol ester, lanolin fatty acid alkanol amide, lanolin fatty acid soap and the like.

With the above difficulties in mind, the present invention provides non-allergenic lanolin and derivatives thereof by eliminating the allergen from lanolin and derivaties thereof.

This invention will be described more specifically in the following Examples.

EXAMPLE 1

Allergy tests with lanolin and derivatives thereof:
Subjects: 19 Patients with lanolin allergy
Allergy patch tests

| Samples | Positive numbers |
|---|---|
| lanolin wax | 2 |
| liquid lanolin | 2 |
| hydrogenated lanolin | 18 |
| acetylated lanolin | 1 |
| lanolin fatty acid | 2 |
| lanolin alcohol | 17 |
| acetylated lanolin alcohol | 3 |
| ethoxylated-acetylated lanolin alcohol | 0 |

In order to elucidate the components containing the allergen, some allergy tests were made with lanolin and derivatives thereof. It was found that hydrogenated lanolin and lanolin alcohol induce high frequency of occurrence in positive number, and on the other hand lanolin wax and liquid lanolin exhibited a low occurrence.

Acetylation of lanolin is inclined to decrease the number positive tests and this tendency is significant, particularly with regard to a lanolin alcohol. The lanolin alcohol shows a high frequency of occurrence of positive tests in patients, but, exthoxylation thereof decreases the positive number to zero. A lanolin fatty acid is, as pointed out in other reports, fully considered to be contaminated with the lanolin alcohol.

In view of the above results, has been it estimated that an allergen is contained in the alcohol components. Further, the following experiments were made with hydrogenated lanolin as a test substance.

EXAMPLE 2

Separation of hydrogenated lanolin and allergy tests:

| | | |
|---|---|---|
| Separation condition: | Thin layer chromatography | |
| Adsorbent: | FLORISIL having a thickness of 0.25mm | |
| Developer: | Chloroform | |
| Sample: | Hydrogenated lanolin | |
| Spot No. | Rf | Allergy tests |
| 1 | 0.90 | Negative |
| 2 | 0.65 | " |
| 3 | 0.51 | " |
| 4 | 0.38 | Positive |
| 5 | 0.10 | " |
| 6 | 0.04 | " |
| 7 | 0 | " |

The spots having the values of Rf less than 0.38 under the above conditions all showed positive allergy reactions, this meant that an allergen was contained in the spots.

EXAMPLE 3

Separation of lanolin and allergy tests:

| | | |
|---|---|---|
| Separation condition: | Thin layer chromatography | |
| Adsorbent: | FLORISIL having a thickness of 0.25mm | |
| Developer: | Chloroform | |
| Sample: | lanolin | |
| Spot No. | Rf | Allergy tests |
| 1 | 0.79 | Negative |
| 2 | 0.57 | " |
| 3 | 0.51 | " |
| 4 | 0.38 | Positive |
| 5 | 0.10 | " |
| 6 | 0.04 | " |

-continued

| | | |
|---|---|---|
| Separation condition: | Thin layer chromatography | |
| Adsorbent: | FLORISIL having a thickness of 0.25mm | |
| Developer: | Chloroform | |
| Sample: | lanolin | |
| Spot No. | Rf | Allergy tests |
| 7 | 0 | " |

The spots having the values of Rf less than 0.38 under the above conditions all showed positive allergy reactions, clearly indicating that an allergen was contained in the spots. These results are closely similar to those in Example 2 wherein hydrogenated lanolin was used.

EXAMPLE 4

Values of Rf of allergen-containing portion of hydrogenated lanolin:

| | | | | |
|---|---|---|---|---|
| Separation condition: | Thin layer chromatography | | | |
| Adsorbent: | FLORISIL having a thickness of 0.25mm | | | |
| Developer: | (1) Benzene<br>(2) Chloroform | | | |
| Sample: | Allergen-containing portion of hydrogenated lanolin | | | |
| Developing solvent | Values of Rf | | | |
| Benzene | 0.14 | 0.04 | 0.02 | 0 |
| Chloroform | 0.38 | 0.10 | 0.04 | 0 |

An allergen-containing portion of hydrogenated lanolin had a fairly strong polarity, and therefore, it exhibited low values of Rf as above.

EXAMPLE 5

Elimination of the allergen-containing portion from hydrogenated lanolin (1):

| | | | |
|---|---|---|---|
| Separation condition: | column chromatography | | |
| Adsorbent: | FLORISIL | | |
| Column: | 25mmφ, 250mm | | |
| Eluants: | (1) Benzene<br>(2) Chloroform/Ether (8/2)<br>(3) Methanol | | |
| Sample: | 1.5g of Hydrogenated lanolin | | |
| Fractions Eluants | | Allergy tests | Recovery |
| I | Benzene 100ml | Negative | 8% |
| II | Benzene 100ml | " | 4% |
| III | Benzene 100ml | " | 65% |
| IV | Chloroform/Ether (8/2) 300ml | Positive | 19% |
| V | Methanol 300ml | " | 4% |

As seen from the above results, the eluates obtained with benzene showed a negative allergy reaction and the recovery of non-allergenic hydrogenated lanolin came to a total of about 80%.

EXAMPLE 6

Elimination of the allergen-containing portion from hydrogenated lanolin (2).

| | | | |
|---|---|---|---|
| Separation condition: | Reduced distillation | | |
| Sample: | 50g of hydrogenated lanolin | | |
| Distillation conditions | Allergy test | Recovery | Existence of Rf 0.32 portion |
| −164° C./3mm Hg distilled portion | Negative | 20.6% | None |

-continued

| Separation condition: | | Reduced distillation | |
|---|---|---|---|
| Sample: | | 50g of hydrogenated lanolin | |
| Distillation conditions | Allergy test | Recovery | Existence of Rf 0.32 portion |
| Residue | Positive | 79.3% | Appearance |

As seen from the above results, reduced distillation also enabled the separation of an allergen-containing portion. However, the recovery was inferior, though it might be increased by improving the distillation conditions.

EXAMPLE 7

Separation of hydrogenated lanolin and adsorbents:

| | |
|---|---|
| Separation condition: | column chromatography |
| Column: | 25mmφ, 250mm |
| Adsorbents: | FLORISIL, silica gel, alumina |
| Eluant: | n-Hexane |
| Sample: | 1.5g of hydrogenated lanolin |

(Comparison of recoveries achieved by allergy reaction became positive.)

| Adsorbents | Recoveries |
|---|---|
| FLORISIL | 80% |
| Silica gel | 55% |
| Alumina | 45% |

As seen from the above results, the recovery decreased in the order of FLORISIL, silica gel and alumina, and FLORISIL showed a particularly high recovery.

EXAMPLE 8

Separation of hydrogenated lanolin and eluants:

| | |
|---|---|
| Separation condition: | Column chromatography |
| Column: | 25mmφ, 250mm |
| Adsorbent: | FLORISIL |
| Eluants: | n-hexane, benzene, carbon tetrachloride, petroleum ether |
| Sample: | 1.5g of hydrogenated lanolin |

(Recoveries achieved by allergy reaction became positive)

| Eluants | Recoveries |
|---|---|
| N-Hexane | 80% |
| Benzene | 77% |
| Carbon tetrachloride | 70% |
| Petroleum ether | 65% |

As seen from the above results, the eluants of n-hexane and benzene showed relatively high recoveries.

EXAMPLE 9

Separation and purification of lanolin and derivatives thereof:

| | |
|---|---|
| Separation condition: | Column chromatography |
| Column: | 25mmφ, 250mm |
| Adsorbent: | FLORISIL |
| Eluants: | Benzene |
| Samples: | (1) lanolin |
| | (2) hydrogenated lanolin |
| | (3) lanolin alcohol |
| | (4) acetylated lanolin |
| | (5) acetylated lanolin alcohol |

(Recoveries achieved by the substances having 0.38 of Rf in Example 2 eluted out.)

| Samples | Recoveries | Allergy tests |
|---|---|---|
| lanolin | 90% | Negative |
| hydrogenated lanolin | 83% | " |
| lanolin alcohol | 80% | " |
| acetylated lanolin | 95% | " |
| acetylated lanolin alcohol | 92% | " |

As seen from the above results, lanolin and derivatives thereof not containing the portion having 0.38 of Rf in thin layer chromatography (FLORISIL: Developer: chloroform) could be recognized as non-allergenic lanolin and non-allergenic lanolin derivatives.

What is claimed as new and desired to be secured by Letters Patent in the United States is:

1. A non-allergenic lanolin, characterized by not containing any substances having a Rf value of less than 0.38 when subjected to a thin layer chromatography test wherein the adsorbent is magnesium silicate having a thickness of 0.25 mm and the solvent is chloroform.

2. A non-allergenic lanolin, characterized by not containing any substances having an Rf value of less than 0.14 when subjected to a thin layer chromatography test wherein the adsorbent is magnesium silicate having a thickness of 0.25 mm and the solvent is benzene.

3. The lanolin derivative of claim 1 wherein said lanolin is selected from the group consisting of hydrogenated lanolin, acetylated lanolin, lanolin fatty acid, lanolin alcohol, acetylated lanolin alcohol and ethoxylated-acetylated lanolin alcohol.

4. The lanolin derivative of claim 2 wherein said lanolin is selected from the group consisting of hydrogenated lanolin, acetylated lanolin, lanolin fatty acid, lanolin alcohol, acetylated lanolin alcohol and ethoxylated-acetylated lanolin alcohol.

* * * * *